US008021651B2

(12) United States Patent
Hentrich et al.

(10) Patent No.: US 8,021,651 B2
(45) Date of Patent: Sep. 20, 2011

(54) PULVERULENT STYLING COMPOSITION

(75) Inventors: Dirk Hentrich, Hamburg (DE); Bernd Richters, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 12/103,581

(22) Filed: Apr. 15, 2008

(65) Prior Publication Data

US 2008/0233071 A1     Sep. 25, 2008

Related U.S. Application Data

(63) Continuation of application No. PCT/EP2006/009515, filed on Sep. 30, 2006.

(30) Foreign Application Priority Data

Nov. 2, 2005 (DE) .......................... 10 2005 052 585

(51) Int. Cl.
*A61Q 5/08* (2006.01)

(52) U.S. Cl. ............. 424/70.15; 424/70.11; 424/70.122; 132/203

(58) Field of Classification Search ........................ None
See application file for complete search history.

(56) References Cited

U.S. PATENT DOCUMENTS

| 5,776,240 A | 7/1998 | Deller et al. | |
|---|---|---|---|
| 2002/0176836 A9 * | 11/2002 | Belli et al. | 424/70.16 |
| 2003/0086886 A1 * | 5/2003 | Midha | 424/70.2 |
| 2005/0169866 A1 | 8/2005 | Hannich et al. | |
| 2005/0255134 A1 | 11/2005 | Hasenzahl et al. | |

FOREIGN PATENT DOCUMENTS

| EP | 1235554 | 9/2002 |
|---|---|---|
| WO | WO0137800 | 5/2001 |
| WO | WO03037287 | 5/2003 |

OTHER PUBLICATIONS

Hasenzahl et al, Fumes silica for personal care and cosmetics—versatile and effective SÖFW—Journal Seifen Öle, Fette, Wachse, Verlag Für chemische Industrie Augsburg, DE, Aug. 2003. Seiten 1 bis 8.
Cosmetic Powder obtd. Using Hydrophobic Silicate—Water and Lubricant e.g., nylon or polyethylene powder, provides a cooling feeling. Derwent 1983 XP-002276355.
International Cosmetic Ingredient Dictionary and Handbook, 7th Ed., (1997), The cosmetic, Toiletry and Fragrance Association 1101 17th Street., N.W., Suite 300, Washington, DC 20036-4702.

* cited by examiner

*Primary Examiner* — Jyothsna Venkat
(74) *Attorney, Agent, or Firm* — David P. LeCroy

(57) ABSTRACT

A pulverulent composition comprising 50 to 95% by weight of an aqueous solvent, hydrophobicized silicon dioxide powder and at least one film-forming and/or setting polymer for the temporary shaping of keratin fibers and a corresponding pulverulent styling composition. Upon mechanical stress, the powder releases the solvent and the film-forming and/or setting polymer so that the desired shaping or setting of, for example, a mechanically produced shape of the treated fibers is achieved.

6 Claims, No Drawings

PULVERULENT STYLING COMPOSITION

CROSS-REFERENCE TO RELATED APPLICATIONS

This application is a continuation under 35 U.S.C. Section 365(c) and 35 U.S.C. Section 120 of International Application No. PCT/EP2006/009515, filed Sep. 30, 2006. This application also claims priority under 35 U.S.C. Section 119 of German Patent Application No. DE 10 2005 052 585.7, filed Nov. 2, 2005. Both the International Application and the German Application are incorporated herein by reference in their entireties.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

The present invention relates to the use of a pulverulent composition based on a hydrophobized silicon dioxide powder as a styling composition for the temporary deformation of keratin fibers and to a corresponding pulverulent styling composition.

Styling compositions for deforming keratin fibers have long been known and are used in various developments for volumizing, reviving and fixing of hairstyles, which with many hair types can only be achieved using setting active ingredients. Both hair treatment compositions which serve to shape hair permanently and those which shape it temporarily play an important role in this respect. Temporary shaping, which is intended to provide a good hold without impairing the healthy appearance of the hair, such as, for example, the gloss thereof, may be achieved, for example, by hairsprays, hair waxes, hair gels, setting lotions etc.

Appropriate compositions for temporary shaping conventionally contain synthetic polymers as the shaping component. Preparations which contain a dissolved or dispersed polymer may be applied to the hair by means of propellant gases or by a pump mechanism. Hair gels and hair waxes, on the other hand, are not generally applied to the hair, but rather are distributed in the hair by means of a comb or the hands.

Known forms of temporary styling compositions often cannot be dispensed with satisfactory accuracy. Thus, for instance, hair gels, hair creams and hair waxes are difficult to distribute once they have been applied to the hair. As soon as the comb or the hands onto which the styling composition has been applied come(s) into contact with the first bits of hair, comparatively large quantities of styling composition are released onto the hair. On the other hand, comparatively little styling composition is worked into bits of hair which are reached only later with the comb or the hands. The consequence of this is that the person applying the composition has either from the outset to apply a large quantity of styling composition, such that even those bits of hair which are reached last receive enough styling composition, or is obliged to apply the styling composition in a number of steps, treating different bits of hair each time. Hairsprays can be applied to hair more uniformly. However, since the user has no possibility of seeing the total quantity of styling composition applied, there is a risk of more styling composition being applied to the hair than is really necessary.

In addition, known types of temporary styling composition generally require a large quantity of auxiliary substances, which serve not actually to fashion the hairstyle but rather in the formulation of the respective composition. The styling compositions thus often contain large quantities of organic solvent. Formulation as hairspray additionally requires further organic compounds, which are used as propellants. This has the effect, on the one hand, that the environment is polluted with volatile organic compounds (VOC) and, on the other hand, that the product volume and thus the volume of the packaging required is increased significantly.

Accordingly, the object of the present invention was to provide a hair treatment composition for temporary shaping which, on the one hand, gives rise to an excellent and durable styling result, and, on the other hand, is present in a maximally compact form and may be dispensed easily and accurately.

It has now been found that this can be achieved simply by a styling composition which is present in powder form.

DESCRIPTION OF RELATED ART, INCLUDING INFORMATION DISCLOSED UNDER 37 C.F.R. SECTIONS 1.97 AND 1.98.

Pulverulent cosmetics are known and have already long been used, for instance, in the field of skin treatment. Typical examples are powder foundation or eyeshadow. To achieve the pulverulent consistency, it is necessary to use a pulverulent carrier material. Silicon dioxide may be used as a suitable carrier material. Hydrophobized silicon dioxide is of particular interest. This may be obtained, for example, on the basis of pyrogenic silicon dioxide, which is obtainable commercially in different specifications. Untreated pyrogenic silicon dioxide bears silanol and siloxane groups on its surface. This gives it a high affinity for water, i.e., it is hydrophilic. Through reaction with suitable organic silicon compounds, alkylsilyl groups may be chemically bound onto the surface of pyrogenic silicon dioxide. Modified silicon dioxide powders, which are no longer wetted by water, i.e., have hydrophobic properties, are obtained.

"Seifen, Öle, Fette, Wachse (SÖFW) ["Soaps, Oils, Fats, Waxes"], 3 (2004), describes on pp. 4-13 the use of hydrophobized silicon dioxide in cosmetics to produce so-called "dry water" for the skin. Here, the hydrophobic properties of the modified silicon dioxide are exploited, which have the effect of ensuring that the silicon dioxide is not readily dispersed in water when mixed intensively therewith. Instead, the water droplets are enclosed by the hydrophobic solid particles and prevented from coalescing again. Pulverulent solids with a water content of up to over 95% may be obtained in this manner. On exposure to mechanical stress, for example, on rubbing onto the skin, the enclosed water is released again. This dry water is described as the basis for the production of storage-stable solid hydrogen peroxide and of spreadable preparations with very low oil content.

This concept also forms the basis of the production described in European Patent Application No. EP 1 235 554 B1 of cosmetic or pharmaceutical, liquefiable powder compositions. The powder compositions comprise hydrophobically coated silicon dioxide particles, in which water and a water-soluble polymer are enclosed, the compositions containing less than 1% oil. Through addition of the water-soluble polymer, it is intended to ensure that the powder feels pleasant and not granular on application to the skin without necessitating the addition of an oil component to the product for this purpose. For this purpose, the polymer is added to the aqueous phase in a quantity of 0.01 to 5 wt. %, a content of merely 0.1 to 1 wt. % being preferred. The liquefiable powder compositions are primarily used to produce decorative cosmetics. A description is also given of use in deodorants or sunscreen preparations, or application to hair as a base for hair treatment compositions containing pearlescent agents or conditioning components. Use in the field of styling compositions is not mentioned.

Published International Application No. WO 03/037287 A1 discloses the use a granular product based on pyrogenic silicon dioxide in cosmetic compositions. The special granules may be silanized, i.e., hydrophobized, and are suitable for the production of cosmetic compositions of any consistency, for example liquids, foams, sprays, or powders. A number of feasible cosmetics, inter alia, hair styling compositions, are mentioned as possible cosmetic compositions. However, only the conventional application forms of lotion, hairspray, hair lacquer, hair gel and hair wax are mentioned in this respect. There is no suggestion that pulverulent styling compositions could be produced on the basis of the above-described silicon dioxide.

BRIEF SUMMARY OF THE INVENTION

Accordingly, the present invention principally provides the use of a pulverulent composition containing 50 to 95 wt. % of an aqueous solvent, hydrophobized silicon dioxide powder and at least one film-forming and/or setting polymer for the temporary deformation of keratin fibers.

According to the invention, keratin fibers should be understood to mean furs, wool, feathers and, in particular, human hair.

The pulverulent compositions may be dispensed very simply. Additionally, they may be distributed very uniformly in the hair, since the solvent and the film-forming and/or setting polymer are only released on exposure to mechanical stress. The powder may thus initially be distributed carefully in the hair and only then be subjected to more severe mechanical loads, for example, by purposeful rubbing of the powder into the hair. In this way, the polymer which provides hold is only released directly onto the desired bit of hair. Thus, an excellent styling effect may be achieved in a highly targeted manner.

BRIEF DESCRIPTION OF THE SEVERAL VIEWS OF THE DRAWING(S)

Not Applicable

DETAILED DESCRIPTION OF THE INVENTION

Preferably, a pulverulent composition is used which contains 70 to 90 wt. %, particularly preferably 80 to 90 wt. % of an aqueous solvent, relative to the total composition.

An aqueous solvent is here understood to mean water or a mixture of water and a $C_1$-$C_4$ alcohol, in particular ethanol. Since, however, under certain circumstances surface-active substances and alcohols wet hydrophobized silicon dioxide and may thus have a negative influence on the hydrophobic properties, it may be necessary, depending on the type of hydrophobized silicon dioxide used, to keep the content of $C_1$-$C_4$ alcohol in the aqueous solvent below a critical maximum quantity.

Preferably, therefore, water or a mixture of water and at most 60 wt. % $C_1$-$C_4$ alcohol, relative to the solvent mixture, is used as the aqueous solvent. Particularly preferred aqueous solvents are water or a mixture of water and at most 30 wt. % $C_1$-$C_4$ alcohol, relative to the solvent mixture. Water is very particularly preferably used.

The pulverulent compositions used contain hydrophobized silicon dioxide. The type of hydrophobized silicon dioxide is not limited in principle, provided that it is ensured that a pulverulent product arises in the event of intensive mixing with the aqueous solvent, containing at least one film-forming and/or setting polymer and optionally further constituents.

Suitable hydrophobized silicon dioxides are known and are described, for example, in Seifen, Öle, Fette, Wachse (SÖFW) ["Soaps, Oils, Fats, Waxes"], 3 (2004), pp. 4-13, EP 1 235 554 B1, WO 03/037287 A1 and EP 0 725 037 B1.

Preferably, hydrophobized silicon dioxides are used, which are obtained by the silanization of pyrogenic silicon dioxide.

Preference is given to those hydrophobized silicon dioxides which have a BET specific surface area of between 10 and 400, preferably between 80 and 300 $m^2/g$.

A number of suitable hydrophobized silicon dioxides are commercially obtainable. Mention may be made by way of example of Aerosil® R104V, Aerosil® R106, Aerosil® R202, Aerosil® R805, Aerosil® R812, Aerosil® R812S, Aerosil® R972 and Aerosil® R8200, all made by Degussa, and HDK® H2000, HDK® H2050 and HDK® H3004, all made by Wacker.

It is particularly preferred to use the hydrophobized silicon dioxides which are obtainable under the names Aerosil® R202, Aerosil® R812S or Aerosil® R972. Very particularly, preference is given to the use of the silicon dioxide with the INCI name silica silylate, which is sold by Degussa under the name Aerosil® R812S.

The pulverulent compositions used contain the hydrophobized silicon dioxide powder preferably in a quantity of 0.5 to 15 wt. %, relative to the total pulverulent composition. The ideal quantity depends above all on the hydrophobicity of the silicon dioxide powder used. The more hydrophobic the silicon dioxide powder, the less is needed thereof in order to obtain a stable, pulverulent product. The comparatively hydrophobic silicon dioxide which is sold by Degussa under the name Aerosil® R812S is, for example, particularly preferably used in a quantity of 3 to 8 wt. % relative to the total pulverulent composition, while the less hydrophobic silicon dioxide Aerosil® R972 is used in a quantity of 10 to 15 wt. % relative to the total pulverulent composition.

The pulverulent composition used contains as a further essential component at least one film-forming and/or setting polymer.

The film-forming and/or setting polymer is contained in the pulverulent composition preferably in a quantity of 1 to 15 weight percent, particularly preferably from 5.5 to 15 weight percent, very particularly preferably in a quantity of 6 to 10 weight percent, relative to the total pulverulent composition. It goes without saying that a plurality of film-forming and/or setting polymers may also be contained therein. In this respect, these film-forming and/or setting polymers may be both permanently and temporarily cationic, anionic, nonionic or amphoteric. When using at least two film-forming and/or setting polymers, it goes without saying that these may have different charges. It may be preferable according to the invention for an ionic film-forming and/or setting polymer to be used together with an amphoteric and/or nonionic film-forming and/or setting polymer. The use of at least two oppositely charged film-forming and/or setting polymers is also preferred. In the latter case, a particular embodiment may in turn additionally contain at least one further amphoteric and/or nonionic film-forming and/or setting polymer.

Since polymers are often multifunctional, their functions cannot always be clearly and unambiguously delimited from one another. This is particularly true of film-forming and setting polymers. Many polymers which have primarily been described as film-forming also have setting properties and vice versa. Therefore, it should be explicitly stated at this point that both film-forming and setting polymers are essential for the purposes of the present invention. Since the two properties are not wholly mutually independent, the term "setting polymers" should always be understood also to mean "film-forming polymers" and vice versa.

The preferred properties of film-forming polymers include film formation. Film-forming polymers should be understood to mean those polymers which, on drying, leave behind a continuous film on the skin, hair or nails. Such film formers may be used in the most varied of cosmetic products, such as, for example, face masks, make-up, hair fixatives, hairsprays, hair gels, hair waxes, hair tonics, shampoos or nail polishes. Particular preference is given to those polymers which have sufficient solubility in water, alcohol or water/alcohol mixtures. Thus, corresponding solutions may be produced which may be simply applied or further processed. The film-forming polymers may be of synthetic or natural origin.

Film-forming polymers are further understood to mean those polymers which are capable, when applied in a 0.01 to 20 wt. % aqueous, alcoholic or aqueous/alcoholic solution, of depositing a transparent polymer film on the hair. The film-forming polymers may be charged in any one of an anionic, amphoteric, nonionic, permanently cationic or temporarily cationic manner.

Suitable synthetic, film-forming, hair-setting polymers preferably used according to the invention are homo- or copolymers, which are composed of at least one of the following monomers: vinylpyrrolidone, vinyl caprolactam, vinyl ester such as, for example, vinyl acetate, vinyl alcohol, acrylamide, methacrylamide, alkyl- and dialkylacrylamide, alkyl- and dialkylmethacrylamide, alkyl acrylate, alkyl methacrylate, propylene glycol or ethylene glycol, the alkyl groups of these monomers preferably being $C_1$ to $C_7$ alkyl groups, particularly preferably $C_1$ to $C_3$ alkyl groups.

Examples which may be mentioned are homopolymers of vinyl caprolactam, vinylpyrrolidone or N-vinylformamide. Examples of further suitable synthetic film-forming, hair-setting polymers are copolymers of vinylpyrrolidone and vinyl acetate, terpolymers of vinylpyrrolidone, vinyl acetate and vinyl propionate, polyacrylamides, which are sold, for example, by CHEM-Y, Emmerich under the trade name Akypomine® P 191, or by Seppic under the trade name Sepigel 305®; polyvinyl alcohols, which are sold, for example, by DuPont under the trade name Elvanol® or by Air Products under the trade name Vinol® 523/540 as well as polyethylene glycol/polypropylene glycol copolymers, which are sold, for example, by Union Carbide under the trade name Ucon®.

Examples of suitable natural film-forming polymers are cellulose derivatives, for example, hydroxypropylcellulose with a molecular weight of 30,000 to 50,000 g/mol, which is sold, for example, by Lehmann & Voss, Hamburg under the trade name Nisso SI®.

Setting polymers assist in holding or building up the volume and fullness of the overall hairstyle. These so-called setting polymers are simultaneously also film-forming polymers and therefore generally typical substances for shaping hair treatment compositions such as hair fixatives, hair mousses, hair waxes, and hairsprays. Film formation may in this respect take place only at points and connect only a few fibers together.

Substances which additionally lend the hair hydrophobic properties are preferred here, because they reduce the tendency of the hair to absorb moisture, i.e., water. This reduces the tendency of hair strands to hang down limply and thus ensures that a hairstyle retains its structure for a long time. The "curl retention" test is often used as a test method in such cases. These polymeric substances may additionally be successfully incorporated into leave-on and rinse-off hair tonics or shampoos. Since polymers are often multifunctional, i.e., have a plurality of effects which are desirable with regard to application, many polymers are to be found in a plurality of groups classified according to their particular mode of action, such as in the CTFA Handbook. Because of the significance specifically of the setting polymers, these will be listed below explicitly by their INCI names. It goes without saying that this list also includes the stated film-forming polymers.

Examples of conventional film-forming, setting polymers are acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates copolymer, acrylates/C1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethyl propanediol-acrylates/acrylamide copolymer, aminoethylpropanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethylmethacrylate copolymer, bacillus/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycol-amine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/P PG-25/25 dimethicone/acrylates copolymer, PEG-8/SMDI copolymer, polyacrylamide, polyacrylate-6, polybeta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhydrophenanthrene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-45, polyquaternium-46, polyquaternium-47, polyquaternium-48, polyquaternium-49, polyquaternium-50, polyquaternium-55, polyquaternium-56, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVP/VA/itaconic acid copolymer, PVPNA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxy-benzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/VA copolymer, VP/vinyl caprolactam/DMAPA acrylates copolymer, yeast palmitate.

Preferably, pulverulent compositions are used according to the invention which contain at least one film-forming and/or setting polymer which is selected from vinylpyrrolidone/vinyl acetate copolymers, vinyl acetate/crotonic acid copolymers, vinyl caprolactam/vinylpyrrolidone/dimethylaminoethyl methacrylate copolymers, octylacrylamide/acrylate/butylaminoethylmethacrylate copolymers and quaternized vinylpyrrolidone/dimethylaminoethyl methacrylate copolymers.

Particularly preferably, the film-forming and/or setting polymers are the vinylpyrrolidone/vinyl acetate copolymers Luviskol® VA 37 or PVP/VA copolymer 60/40 W NP, the vinyl acetate/crotonic acid copolymer sold under the tradename Aristoflex® A 60, the vinyl caprolactam/vinylpyrrolidone/dimethylaminoethyl methacrylate copolymer with the trade name Advantage® LC-E, the amphoteric octylacrylamide/acrylate/butylaminoethyl/methacrylate copolymer obtainable under the name Amphomer® or the vinylpyrrolidone/dimethylaminoethyl methacrylate copolymer quaternized by reaction with diethyl sulfate and sold under the tradename Gafquat® 755N.

It is particularly preferable for pulverulent compositions to be used which contain at least one vinylpyrrolidone/vinyl acetate copolymer.

The pulverulent composition used may further contain the auxiliary substances and additives which are usually added to conventional styling compositions.

Suitable auxiliary substances and additives include, in particular, conditioning substances.

An example of a conditioning substance which may be used is a silicone oil and/or a silicone gum.

Silicone oils or silicone gums suitable according to the invention are, in particular, dialkyl- and alkylarylsiloxane, such as, for example, dimethylpolysiloxane and methylphenylpolysiloxane, and the alkoxylated, quaternized or also anionic derivatives thereof. Preference is given to cyclic and linear polydialkylsiloxanes, the alkoxylated and/or aminated derivatives thereof, dihydroxypolydimethylsiloxanes and polyphenylalkylsiloxanes.

Silicone oils have a very wide range of effects. For example, they simultaneously influence dry and wet combability, the feel of the dry and wet hair and its gloss. The term "silicone oils" is understood by the person skilled in the art to mean a plurality of organo-silicon compounds of different structures. These include first of all dimethiconols and dimethicones, for instance the PEG-12 dimethicone sold by Dow Corning under the name Dow Corning® 193 Surfactant. These may be both linear and branched and cyclic or cyclic and branched. Also included are dimethicone copolyols, as sold, for example, by Dow Corning under the name Dow Corning® 5330 Fluid, and aminofunctional silicones, in particular, the silicones covered by the INCI name amodimethicone.

A cationic surfactant may also be used as a conditioner. In this respect, preference is given to cationic surfactants of the type including quaternary ammonium compounds, ester quats and the amidoamines. Preferred quaternary ammonium compounds are ammonium halides, in particular, chlorides and bromides, such as alkyltrimethylammonium chlorides, dialkyldimethylammonium chlorides and trialkylmethylammonium chlorides, for example, cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and imidazolium compounds known by the INCI names quaternium-27 and quaternium-83. The long alkyl chains of the above-stated surfactants preferably comprise 10 to 18 carbon atoms. Since, however, the addition of surface-active substances may have a negative effect on the hydrophobic properties of the hydrophobized silicon dioxide and thus on the stability of the pulverulent compositions used, the quantity of conditioning surfactant has to be carefully matched to the total composition. Preferably, no surfactant constituents are added.

Conditioning polymers are likewise suitable as conditioners.

A first group of conditioning polymers comprises cationic polymers. Cationic polymers are polymers which comprise a group in the main and/or side chain which may be "temporarily" or "permanently" cationic. Polymers which are designated "permanently cationic" according to the invention are those which, irrespective of pH value, comprise a cationic group. As a rule, these are polymers which contain a quaternary nitrogen atom, for example, in the form of an ammonium group. Preferred cationic groups are quaternary ammonium groups. Polymers which have proven particularly suitable are those in which the quaternary ammonium group is bound via a $C_{1-4}$ hydrocarbon group to a main polymer chain synthesized from acrylic acid, methacrylic acid or the derivatives thereof.

A particularly suitable homopolymer is poly(methacryloyloxyethyltrimethylammonium chloride), which may, if desired, be crosslinked, with the INCI name of polyquaternium-37. Crosslinking may, if desired, proceed with the assistance of olefinically polyunsaturated compounds, for example, divinylbenzene, tetraallyloxyethane, methylenebisacrylamide, diallyl ether, polyallyl polyglyceryl ether, or allyl ethers of sugars or sugar derivatives such as erythritol, pentaerythritol, arabitol, mannitol, sorbitol, sucrose or glucose. Methylenebisacrylamide is a preferred crosslinking agent.

Cationic polymers additionally include protein hydrolyzates, wherein the underlying protein hydrolyzate may originate from animals, for example, from collagen, milk or keratin, from plants, for example, from wheat, maize, rice, potatoes, soya or almonds, from marine life forms, for example, from fish collagen or algae, or biotechnologically obtained protein hydrolyzates. The protein hydrolyzates underlying the cationic derivatives according to the invention may be obtained from the corresponding proteins by chemical, in particular, alkaline or acidic, hydrolysis, by enzymatic hydrolysis and/or by a combination of both types of hydrolysis. Protein hydrolysis as a rule gives rise to a protein hydrolyzate with a molecular weight distribution of approximately 100 daltons up to several thousand daltons. Those cationic protein hydrolyzates are preferred whose underlying protein fraction has a molecular weight of 100 up to 25,000 daltons, preferably 250 to 5,000 daltons. Furthermore, cationic protein hydrolyzates include quaternized amino acids and mixtures thereof. Quaternization of the protein hydrolyzates or of the amino acids is often performed by means of quaternary ammonium salts such as, for example, N,N-dimethyl-N-(n-alkyl)-N-(2-hydroxy-3-chloro-n-propyl)-ammonium halides. The cationic protein hydrolyzates may additionally also be still further derivatized. Typical examples of the cationic protein hydrolyzates and derivatives according to the invention which may be mentioned are those that are commercially obtainable and mentioned under the INCI names in the "International Cosmetic Ingredient Dictionary and Handbook", (Seventh edition 1997, The Cosmetic, Toiletry, and Fragrance Association 1101 17th Street, N.W., Suite 300, Washington, D.C. 20036-4702): cocodimonium hydroxypropyl hydrolyzed collagen, cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed soy protein, cocodimonium hydroxypropyl hydrolyzed wheat protein, hydroxypropyl arginine lauryl/myristyl ether HCl, hydroxypropyltrimonium gelatin, hydroxypropyltrimonium hydrolyzed casein, hydroxypropyltrimonium hydrolyzed collagen, hydroxypropyltrimonium hydrolyzed conchiolin protein, hydroxypropyltrimonium hydrolyzed keratin, hydroxypropyltrimonium hydrolyzed rice bran protein, hydroxypropyltrimonium hydrolyzed soy protein, hydroxypropyl hydrolyzed vegetable protein, hydroxypropyltrimonium hydrolyzed wheat protein, hydroxypropyltrimonium hydrolyzed wheat protein/siloxysilicate, laurdimonium hydroxypropyl hydrolyzed soy protein, laurdimonium hydroxypropyl hydrolyzed wheat protein, laurdimonium hydroxypropyl hydrolyzed wheat protein/siloxysilicate, lauryldimonium hydroxypropyl hydrolyzed casein, lauryldimonium hydroxypropyl hydrolyzed collagen, lauryldimonium hydroxypropyl hydrolyzed keratin, lauryldimonium hydroxypropyl hydrolyzed soy protein, steardimonium hydroxypropyl hydrolyzed casein, steardimonium hydroxypropyl hydrolyzed collagen, steardimonium hydroxypropyl hydrolyzed keratin, steardimonium hydroxypropyl hydrolyzed rice protein, steardimonium hydroxypropyl hydrolyzed soy protein, steardimonium hydroxypropyl hydrolyzed vegetable protein, steardimonium hydroxypropyl hydrolyzed wheat protein, steartrimonium hydroxyethyl hydrolyzed collagen, quaternium-76 hydrolyzed collagen, quaternium-79 hydrolyzed collagen, quaternium-79 hydrolyzed keratin, quaternium-79 hydrolyzed milk protein, quaternium-79 hydrolyzed soy protein, quaternium-79 hydrolyzed wheat protein.

Plant-based cationic protein hydrolyzates and derivatives are preferred.

Further conditioning polymers which may be used according to the invention are amphoteric polymers.

Moreover, at least one vitamin, one provitamin, one vitamin precursor and/or one of the derivatives thereof may be used as conditioner.

Those vitamins, provitamins and vitamin precursors are preferred according to the invention which are conventionally assigned to the groups A, B, C, E, F and H. Vitamins are particularly preferred which belong to the B group or to the vitamin B complex, very particularly preferably vitamin $B_5$ (pantothenic acid, panthenol and pantolactone).

At least one plant extract may further be used as a conditioner.

Conventionally, these extracts are provided by extraction of the entire plant. However, in individual cases it may also be preferable to produce the extracts solely from the blossoms and/or leaves of the plant.

With regard to the plant extracts preferred according to the invention, particular reference is made to the extracts which are listed in the table starting on page 44 of the 3rd edition of the "Leitfaden zur Inhaltsstoffdeklaration kosmetischer Mittel" ["Guidelines for the nomenclature of ingredients in cosmetic agents"], published by the German Cosmetic, Toiletry, Perfumery and Detergent Association (IKW), Frankfurt.

According to the invention, the highest preference is given to extracts from water lily, green tea, oak bark, stinging nettle, witch hazel, hops, henna, chamomile, burdock root, horsetail, hawthorn, lime blossom, almond, aloe vera, pine-needle oil, horse chestnut, sandalwood, juniper, coconut, mango, apricot, lime, wheat, kiwi, melon, orange, grapefruit, sage, rosemary, birch, mallow, lady's smock, wild thyme, yarrow, thyme, melissa, restharrow, coltsfoot, marsh mallow, meristem, ginseng and ginger root.

Also suitable as conditioner are a series of carboxylic acids.

Short-chain carboxylic acids, in particular, may be advantageous for the purposes of the invention. For the purposes of the invention, short-chain carboxylic acids and the derivatives thereof are understood to mean carboxylic acids which may be saturated or unsaturated and/or linear or branched or cyclic and/or aromatic and/or heterocyclic and have a molecular weight of less than 750. Preference may be given, for the purposes of the invention, to saturated or unsaturated linear or branched carboxylic acids with a chain length of from 1 up to 16 C atoms in the chain, very particular preference being given to those with a chain length of from 1 up to 12 C atoms.

Further suitable conditioners are protein hydrolyzates and/or the derivatives thereof, the use of protein hydrolyzates of plant origin, for example, soy, almond, pea, potato and wheat protein hydrolyzates being preferred. Such products are obtainable, for example, under the trade names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Although the use of protein hydrolyzates as such is preferred, amino acid mixtures obtained in other ways may also optionally be used in their stead. Likewise possible is the use of derivatives of protein hydrolyzates, for example, in the form of the fatty acid condensation products thereof. Such products are sold, for example, under the names Lamepon® (Cognis), Lexein® (Inolex), Crolastin® (Croda), Crosilk® (Croda) or Crotein® (Croda).

It goes without saying that the teaching according to the invention comprises all isomeric forms, such as cis-trans isomers, diastereomers and chiral isomers.

According to the invention, it is also possible to use a mixture of several protein hydrolyzates.

Furthermore, lipids and oil bodies are suitable as conditioners, for example, plant oils, liquid paraffin oils, isoparaffin oils, synthetic hydrocarbons and ester oils, enzymes and pearl extracts.

Further auxiliary substances and additives may also be added in addition to the conditioners.

Through the addition of a UV filter, both the preparations themselves and the treated fibers may be protected from the harmful effects of UV radiation. Therefore, it may be advantageous to add at least one UV filter to the pulverulent preparations. The suitable UV filters are not subject to any general restrictions with regard to structure and physical properties. Rather, any UV filters usable in the field of cosmetics whose absorption maximum is in the UVA (315-400 nm), the UVB (280-315 nm) or the UVC (<280 nm) range are suitable. UV filters with an absorption maximum in the UVB range, in particular in the range from approximately 280 to approximately 300 nm, are particularly preferred.

The UV filters preferred according to the invention may, for example, be selected from substituted benzophenones, p-aminobenzoic acid esters, diphenylacrylic acid esters, cinnamic acid esters, salicylic acid esters, benzimidazoles and o-aminobenzoic acid esters. Examples which may be mentioned here are 2-hydroxy-4-methoxybenzophenone-5-sulfonic acid and the sodium salt thereof (benzophenone-4; Uvinul®MS 40; Uvasorb®S 5).

In one particular embodiment, the pulverulent composition used further comprises one or more direct dyes. This makes it possible, when applying the composition, for the treated keratin fibers not only to be temporarily structured but also to be dyed at the same time. This may be particularly desirable when only temporary dyeing, for example, with conspicuous fashion colors, is desired, which may be removed again from the keratin fiber simply by washing.

The addition of a surfactant is also not ruled out, but it is not preferred due to the above-mentioned disadvantageous influence on the hydrophobicity of the silicon dioxide and thus the stability of the pulverulent composition.

On the other hand, it may be advantageous, in particular, for increasing the stability of the pulverulent composition, to add thickeners such as agar agar, guar gum, alginates, xanthan gum, gum arabic, gum karaya, locust bean flour, linseed gums, dextrans, cellulose derivatives, for example, methylcellulose, hydroxyalkylcellulose and carboxymethylcellulose, starch fractions and derivatives such as amylose, amylopectin and dextrins, clays such as, for example, bentonite or fully synthetic hydrocolloids, such as, for example, polyvinyl alcohol.

The conventional addition of perfume components and preservatives is also possible.

The pulverulent compositions may further contain alkalizing agents, conventionally alkali metal or alkaline earth metal hydroxides, ammonia or organic amines. Preferred alkalizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanolamine and alkali metal and alkaline earth metal hydroxides. In particular, monoethanolamine, triethanolamine and 2-amino-2-methylpropanol and 2-amino-2-methyl-1,3-propanediol are preferred in the context of this group. ω-Amino acids such as ω-aminocaproic acid may also be used as alkalizing agents.

The pulverulent compositions which are used according to the invention for temporary deformation of keratin fibers are simple to produce. It has proven effective to produce, for instance by simple stirring, an aqueous solution or dispersion of the film-forming and/or setting polymer and the desired auxiliary substances and additives, to place this in a mixer and finally to add the hydrophobized silicon dioxide powder with intensive stirring. The necessary mixing period is dependent on the mixing energy introduced and the particular composition of the mixture, but as a rule amounts to between 15 seconds and 5 minutes. If mixing is performed for too short a time, a stable powder does not form and an aqueous phase forms. If the mixing time is excessively long, the initially obtained powder is transformed into a pulpy or creamy consistency, this process proceeding irreversibly. Therefore, it is advisable to determine the optimum mixing period for the particular system through preliminary testing.

The pulverulent compositions may be packaged in virtually any desired container. It has merely to be ensured that, on discharge of the composition, the powder is not exposed to a mechanical load which is so great that the powder is transformed into liquid form as early as the time of discharge. Suitable containers are, for example, jars, bottles or also tetrapacks, the container being designed, for example, with a dispensing and metering device. When using the pulverulent composition for the temporary deformation of keratin fibers, the desired quantity of the pulverulent composition is first discharged from the container. The composition may then be applied directly onto the keratin fibers to be treated or, for example, onto a hand. In the first instance, the applied powder may be exposed to a mechanical load, for example, by means of the hands, directly on the keratin fiber, whereby the solvent and the film-forming and/or setting polymer are released directly onto the fiber. If the pulverulent composition is initially discharged onto the hand, it may first be carefully distributed in the hair and only then be exposed to a more severe mechanical load, for example, by purposeful rubbing in of the powder into the hair. In this way, the polymer which provides hold is only released directly onto the desired bit of hair. In this way, an excellent styling effect may be achieved in a highly targeted manner. It is, of course, also possible to rub the pulverulent composition on the hand and then to apply the resultant liquid or pasty composition onto the keratin fiber. However, this procedure is not preferred, since a significant advantage of the pulverulent consistency of the styling composition, namely the ease with which it may be distributed, is then lost. The pulverulent composition may, of course, also be applied using an auxiliary device, for instance a paintbrush, a sponge, a cloth, a hairbrush or a comb.

The invention secondly provides pulverulent styling compositions containing 50 to 90 wt. % of an aqueous solvent, hydrophobized silicon dioxide powder and 5.5 to 15 wt. % of at least one film-forming and/or setting polymer.

The special and preferred developments of the pulverulent styling composition according to the invention correspond to those already listed above.

The following Examples are intended to explain the subject matter of the present invention without limiting it in any way.

EXAMPLES

Unless otherwise stated, the quantities given below are in weight percent.

1 Production of Liquid Styling Compositions.

First of all, liquid styling compositions A1 to A4 were produced conventionally, these having the following composition:

| Raw materials | A1 | A2 | A3 | A4 |
|---|---|---|---|---|
| Luviskol ® VA 37 E 60 | 8.0 | — | — | 6.0 |
| PVP/VA 60/40 W NP | — | 4.0 | — | — |
| Aristoflex ® A 60 | — | 5.0 | — | — |
| Advantage ® LC-E | — | — | 10.0 | — |
| Gafquat ® 755N | — | — | — | 0.5 |
| Genamin ® CTAC | 0.3 | 0.1 | 0.2 | 0.15 |
| Gluadin ® WQ | — | — | 0.25 | — |
| Gluadin ® WLM | — | — | 0.25 | — |
| Dow Corning ® 193 Surfactant | — | 0.2 | — | — |
| PEG-40 hydrogenated castor oil | — | 0.1 | — | 0.1 |
| Polyethylene glycol (MW 1500) | — | 0.2 | — | 0.6 |
| Herb. extract, water lily COS-241/404-A | — | — | 0.1 | — |
| Solan ® ELD | — | — | 0.2 | — |
| D-Panthenol (75%) | — | — | 0.2 | — |
| Pantolactone | — | — | 0.2 | — |
| Benzophenone-4 | — | — | 0.05 | — |
| Glycine | — | — | 0.2 | — |
| Lactic acid (80%) | — | — | 0.05 | — |
| Perfume | 0.1 | 0.1 | 0.2 | 0.1 |
| Ethanol (96%), denatured | 32.0 | 52.0 | 30.0 | 30.0 |
| Water, deionized | to make up to 100 | to make up to 100 | to make up to 100 | to make up to 100 |

2 Conversion into Pulverulent Compositions According to the Invention 47.5 g of the respective liquid styling composition A1, A2, A3 or A4 were initially introduced into a mixer and combined with stirring with in each case 2.5 g of the hydrophobized silicon dioxide powder Aerosil® R 812 S (INCI name: silica silylate). After a stirring time of in each case 30 to 45 seconds, a stable powder had in each case formed, which was packaged in polyethylene bottles. Pulverulent compositions B1, B2, B3 and B4 were obtained in this way.

3 Application.

For application, in each case the desired quantity of pulverulent compositions B1, B2, B3 or B4 was discharged and distributed carefully into human hair. Then the composition was liquefied by rubbing and kneading, and in this way, the hair was shaped as desired using the hands. An excellent styling result was achieved. Surprisingly, powder residues were not visible in the treated hair nor was an excessive de-lustering effect observed.

4 List of Raw materials Used.

The raw materials used in the context of the Examples are defined as follows:

| | |
|---|---|
| Luviskol ® VA 37 E60 | Vinylpyrrolidone/vinyl acetate copolymer (30:70) (approximately 48-52% solids content in ethanol; INCI name: VP/VA copolymer) (BASF) |
| PVP/VA 60/40 W NP | Vinylpyrrolidone/vinyl acetate copolymer (60:40) (approximately 48 52% solids content in water; INCI name: VP/VA copolymer) (ISP) |
| Aristoflex ® A 60 | Vinyl acetate/crotonic acid copolymer (approximately 60-63% solids content in i-propyl alcohol; INCI name: VA/crotonates copolymer, isopropyl alcohol) (Clariant) |
| Advantage ® | LC-E vinyl caprolactam/vinylpyrrolidone/dimethyl-aminoethyl methacrylate copolymer (approximately 35-39% solids content in ethanol; INCI name: vinyl caprolactam/VP/dimethylaminopropyl methacrylate copolymer, alcohol, lauryl pyrrolidone) (ISP) |
| Gafquat ® 755N | Dimethylaminoethyl methacrylate/vinylpyrrolidone copolymer, quaternized with diethyl sulfate (approximately 19% solids content in water; INCI name: polyquaternium-11) (ISP) |
| Genamin ® CTAC | Trimethylhexadecylammonium chloride (approximately 28-30% active substance in water; INCI name: cetrimonium chloride) (Clariant) |
| Gluadin ® WQ | Wheat protein hydrolyzate (approximately 31-35% solids content; INCI name: aqua (water), laurdimonium hydroxypropyl hydrolyzed wheat protein, ethylparaben, methylparaben) (Cognis) |
| Gluadin ® WLM | Wheat protein hydrolyzate (approximately 21-24% solids content; INCI name: hydrolyzed wheat protein) (Cognis) |
| Dow Corning ® 193 surfactant | Silicone glycol copolymer (INCI name: PEG-12 dimethicone) (Dow Corning) |
| PEG-40 hydrogenated castor oil: | Polyethylene glycol derivative of hydrogenated castor oil with on average 40 mol of ethylene oxide (INCI name: PEG-40 hydrogenated castor oil) (BASF) |
| Solan ® ELD: | Polyethylene glycol derivative of lanolin with on average 75 mol of ethylene oxide (INCI name: PEG-75 lanolin) (Croda) |
| Benzophenone-4 (INCI) | 2-Hydroxy-4-methoxybenzophenone-5-sulfonic acid |

The invention claimed is:
1. A process for temporary deformation of keratin fibers comprising:
   preparing a liquid styling composition comprising
      an aqueous solvent and
      at least one film-forming and/or setting polymer chosen from vinylpyrrolidone/vinyl acetate copolymers, vinyl acetate/crotonic acid copolymers, vinyl caprolactam/vinylpyrrolidone/dimethylaminoethyl methacrylate copolymers, octylacrylamide-acrylate-butylaminoethyl methacrylate copolymers and vinylpyrrolidone/dimethylaminoethyl methacrylate copolymer,
   mixing the liquid styling composition with silica silylate forming a pulverulent composition,
   wherein the pulverulent composition comprises 50 to 95 wt. % of the aqueous solvent, based on total weight of the pulverulent composition, at least one film-forming and/or setting polymer, and silica silylate,
   wherein the silica silylate is present in an amount of 0.5 to 15 wt. %, and
   applying the pulverulent composition to the fibers.

2. The process as claimed in claim 1, wherein the pulverulent composition contains 70 to 90 wt. % of an aqueous solvent.

3. The process as claimed in claim 1, wherein the aqueous solvent is water or a water/ethanol mixture.

4. The process as claimed in claim 1, wherein the pulverulent composition contains 5.5 to 15 wt. % of at least one film-forming and/or setting polymer.

5. The process as claimed in claim 1, wherein the pulverulent composition contains 3 to 8 wt. % of silica silylate.

6. The process as claimed in claim 1 further comprising the step of releasing the aqueous solvent and the film-forming and/or setting polymer on exposure to mechanical stress.

* * * * *